US008540707B2

(12) United States Patent
Sliwa et al.

(10) Patent No.: US 8,540,707 B2
(45) Date of Patent: Sep. 24, 2013

(54) TEMPLATE SYSTEM AND METHODS

(75) Inventors: John W. Sliwa, Los Altos Hills, CA (US); Thomas B. Eby, Mountain View, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1143 days.

(21) Appl. No.: 11/962,478

(22) Filed: Dec. 21, 2007

(65) Prior Publication Data
US 2009/0163910 A1    Jun. 25, 2009

(51) Int. Cl.
*A61B 18/14*  (2006.01)
(52) U.S. Cl.
USPC ............ 606/41; 606/27; 606/28; 606/29; 606/30; 606/31
(58) Field of Classification Search
USPC ............................................. 606/27–31, 41
See application file for complete search history.

(56) References Cited

U.S. PATENT DOCUMENTS

| | | | |
|---|---|---|---|
| 4,757,823 A * | 7/1988 | Hofmeister et al. | 600/437 |
| 5,797,923 A * | 8/1998 | Aiyar et al. | 606/129 |
| 6,361,531 B1 * | 3/2002 | Hissong | 606/27 |
| 6,663,622 B1 * | 12/2003 | Foley et al. | 606/34 |
| 7,223,239 B2 * | 5/2007 | Schulze et al. | 600/439 |
| 2001/0029366 A1 | 10/2001 | Swanson et al. | |
| 2001/0039415 A1 * | 11/2001 | Francischelli et al. | 606/27 |
| 2001/0041902 A1 * | 11/2001 | Lepulu et al. | 606/153 |
| 2002/0082528 A1 * | 6/2002 | Friedman et al. | 601/2 |
| 2002/0143326 A1 * | 10/2002 | Foley et al. | 606/41 |
| 2003/0078571 A1 * | 4/2003 | Sliwa et al. | 606/28 |
| 2004/0034312 A1 | 2/2004 | Koster et al. | |
| 2004/0073206 A1 * | 4/2004 | Foley et al. | 606/34 |
| 2004/0254419 A1 * | 12/2004 | Wang et al. | 600/8 |
| 2005/0154413 A1 * | 7/2005 | Trabada et al. | 606/190 |

FOREIGN PATENT DOCUMENTS

WO    2007/080595 A2    7/2007

OTHER PUBLICATIONS

Drawing Replacement Sheet of Fig. 2 for US Pub. No. 2005/0154413 by Trabada.*

* cited by examiner

*Primary Examiner* — Michael Peffley
*Assistant Examiner* — Khadijeh Vahdat
(74) *Attorney, Agent, or Firm* — Trenner Law Firm, LLC (57) ABSTRACT

Template systems and methods for various procedures (e.g., tissue ablation procedures) are disclosed. An exemplary template system comprises a track having at least one suction port. The at least one suction port anchors the track to a tissue after the track is positioned adjacent a target area. The template system may further comprise a transducer operatively associated with the track. Exemplary transducers include imaging transducers and ablating transducers. The transducer is guided by the track adjacent the target area while the transducer is moved along the track for a procedure. One or more umbilical may provide a conduit to the track and/or transducer so that the template system may be positioned in a patient's body (e.g., for a procedure on the patient's heart) and operated remotely by a physician or other user from outside of the patient's body.

30 Claims, 8 Drawing Sheets

TEMPLATE SYSTEM AND METHODS

BACKGROUND OF THE INVENTION a. Field of the Invention

The instant invention is directed toward a template system and methods for use on a tissue, e.g., for ablation procedures. In particular, the template system of the present invention comprises a track which may be anchored to the tissue, and guides a transducer for ablation and other procedures.

b. Background Art

Normal heart rhythm is between 60 and 100 beats per minute. Tachycardia is a fast heart rate (usually over 100 beats per minute) caused by disease or injury. Tachycardias may begin in the upper chambers of the heart (the atria) or the lower chambers of the heart (the ventricles). Some tachycardias are harmless, but other tachycardias are life threatening. With this disorder, the heart does not fill with enough blood between beats to meet the needs of the body. Tachycardias can quickly deteriorate to fibrillation.

Atrial fibrillation (AF) is the most common abnormal heart rhythm. It is a very fast, uncontrolled heart rhythm that occurs when the upper chambers of the heart (the atria) try to beat so fast (between 350 and 600 times per minute) that they only quiver. Ventricular fibrillation (VF) occurs when the lower chambers of the heart (the ventricles) produce impulses that make the heart beat too quickly. Fibrillation is a life-threatening arrhythmia demanding immediate treatment.

Before a tachycardia deteriorates to fibrillation, various procedures may be used to treat the heart tissue and reduce or altogether eliminate the occurrence of fibrillations. It is well known that treatment benefits may be gained by forming lesions in tissue if the depth and location of the lesions being formed can be controlled. These lesions block the errant electrical signals that result in the tachycardia. In particular, it can be desirable to elevate tissue temperature until thermally necrosed lesions are formed which change, i.e. reduce or eliminate the electrical conductivity of the tissue. For example, when "good" or "sufficiently deep" lesions are formed at specific locations in cardiac tissue, undesirable fibrillations may be lessened or eliminated. The definition of "good" or "sufficiently deep" when describing lesion formation depends at least to some extent on the procedure and may also depend on other considerations, such as tissue characteristics and desired results. In general it is currently thought that transmural lesions are desired (i.e., lesions extending from the endocardium to the epicardium). However some recently reported work demonstrates this may not always be true.

Several difficulties may be encountered with existing ablation or lesion-making techniques. For example, during minimally invasive ablation procedures on a patient's heart, a physician makes a small incision in the patient's abdomen for insertion of an ablation wand. The wand may have a radio-frequency (RF) electrode on the tip for delivering ablative energy to the heart tissue. The physician must maneuver the tip of the wand adjacent the heart tissue to be ablated (the "target area"). The physician may determine placement of the wand based on his/her experience maneuvering the wand during the ablation procedure. Such experience only comes with time, and may be quickly lost if the physician does not perform ablation procedures on a regular basis. In the case of MIS surgery the target tissues are not in the surgeon's direct line of sight.

Even an experienced physician may find it difficult to maneuver the wand. For example, an extended wand inserted through a small incision in the patient's abdomen severely limits the physician's ability to manipulate the tip of the wand in the desired direction near or on the heart. In addition, the axis of the wand may not be aligned with the desired lesion axis, thereby requiring the physician to reposition the wand so that the physician can pull the wand in the direction needed to form a linear or curvilinear lesion. Even after properly positioning the wand, it is often difficult to drag the wand at a constant velocity and at the appropriate angle to achieve a uniformly deep and wide lesion.

When these procedures are performed on the heart, the beating heart further complicates matters by making it difficult to assess placement of the wand adjacent the tissue during the time needed to form the desired lesion. That is to say that one would not want the wand moving uncontrollably, as by random lateral slippage or sliding, during the procedure. If the wand is not properly controlled, a quality lesion is unlikely to be formed and the procedure may be unsuccessful, needing to be repeated to achieve the desired result. In addition, there may be undesirable damage to the surrounding tissue. So lesions are typically made by a stationary or otherwise fixed ablator (relative to the tissue to be ablated) or are made with a controllably scanned or moved ablator. In either case, the energy deposition is predictable for all tissue ablated.

Thus, there remains a need for controlled placement and movement of ablation means during ablation procedures.

BRIEF SUMMARY OF THE INVENTION

It is desirable to be able to control placement and movement of ablation means and other devices during various procedures. This can be accomplished with the template system of the present invention.

The present invention may be implemented in a template system having a track that anchors to the tissue, and a transducer that is guided by the track over the target area during a medical procedure (e.g., ablation procedures). In an exemplary embodiment, the track may be positioned on the tissue using conventional techniques, such as, fluoroscopy or ultrasound imaging, an optical scope, radiopaque markers, etc. Once positioned, the track is anchored to the tissue adjacent the target area and the transducer is guided by the track to perform the desired procedure in a controlled manner, e.g., enabling a physician to form quality lesions during ablation procedures.

In an exemplary embodiment of the present invention, the template system comprises a track having at least one suction port. The suction port anchors the track to a tissue after the track is positioned adjacent a target area. The template system also comprises a transducer operatively associated with the track. The transducer is guided by the track adjacent the target area of the tissue while the transducer is moved along the track for performing a procedure.

The present invention also includes a system comprising guide means for attaching adjacent a target area of a tissue. The system comprises means for anchoring the guide means to the tissue after the guide means is positioned over the target area of the tissue. The system also comprises means for delivering energy to the target area of the tissue while moving along the guide means or at sequential positions along the guide means.

The present invention also includes methods. In an exemplary embodiment, a method comprises: providing a track for anchoring to a tissue after the track is positioned adjacent a target area, and providing a transducer with the track so that the transducer is guided by the track adjacent to the target area for a procedure.

The template system may also include an umbilical attached to the track. The umbilical provides a conduit to the track, e.g., for application of suction to at least one suction port for anchoring the track to the tissue. The template system may also comprise an umbilical attached to the transducer. The umbilical provides a conduit to the transducer, e.g., for delivering ablative or other therapeutic energy, and/or for delivering cooling fluid, flushing fluid, or other fluids. The umbilical may also provide a conduit for at least one guiding or driving wire. The guiding or driving wire may be operable to control movement of the transducer on the track.

The template system may also include means for indexing movement of the transducer relative to the track (e.g., continuous indexing or discrete ablation stepped motion). For example, a gear wheel may be provided on the transducer which may engage a gear strip on the track to move the transducer along the track. Optionally, a drive motor may be implemented to drive the gear wheel on the transducer and move the transducer along the track at a predetermined pace. Although the drive motor is best positioned outside of the patient's body to reduce overall size of the template system, in other embodiments a sufficiently small drive motor may be provided as part of the track or transducer.

The foregoing and other aspects, features, details, utilities, and advantages of the present invention will be apparent from reading the following description and claims, and from reviewing the accompanying drawings.

DETAILED DESCRIPTION OF THE INVENTION

Several embodiments of a template system according to the present invention are depicted in the figures as the template system may be used for lesion formation during a medical procedure. As described further below, the template system of the present invention provides a number of advantages, including, for example, the ability to control and maintain tissue contact and registration during lesion formation on tissue. By tissue contact we mean positional registration and clamping of the track to the tissue, as well as other types of contact (e.g., acoustic contact or coupling of the transducer into the tissue). The template system facilitates more reliable lesion formation, particularly in difficult environments (e.g., the tissue of a beating heart and applications involving ablation while the transducer is being scanned).

Before continuing, it is noted that other components typical of ablation systems which are conventionally implemented for such procedures, are not shown or described herein for purposes of brevity. Such components may nevertheless also be provided as pair of, or for use with, the template system. For example, medical devices for surgical procedures on the heart are commonly used in conjunction with an ECG recording system, associated sensing and/or pacing electrodes, and/or various input and output devices. Such components are well understood in the medical devices arts and therefore further explanation is not necessary for a complete understanding of the invention.

Figure 1:
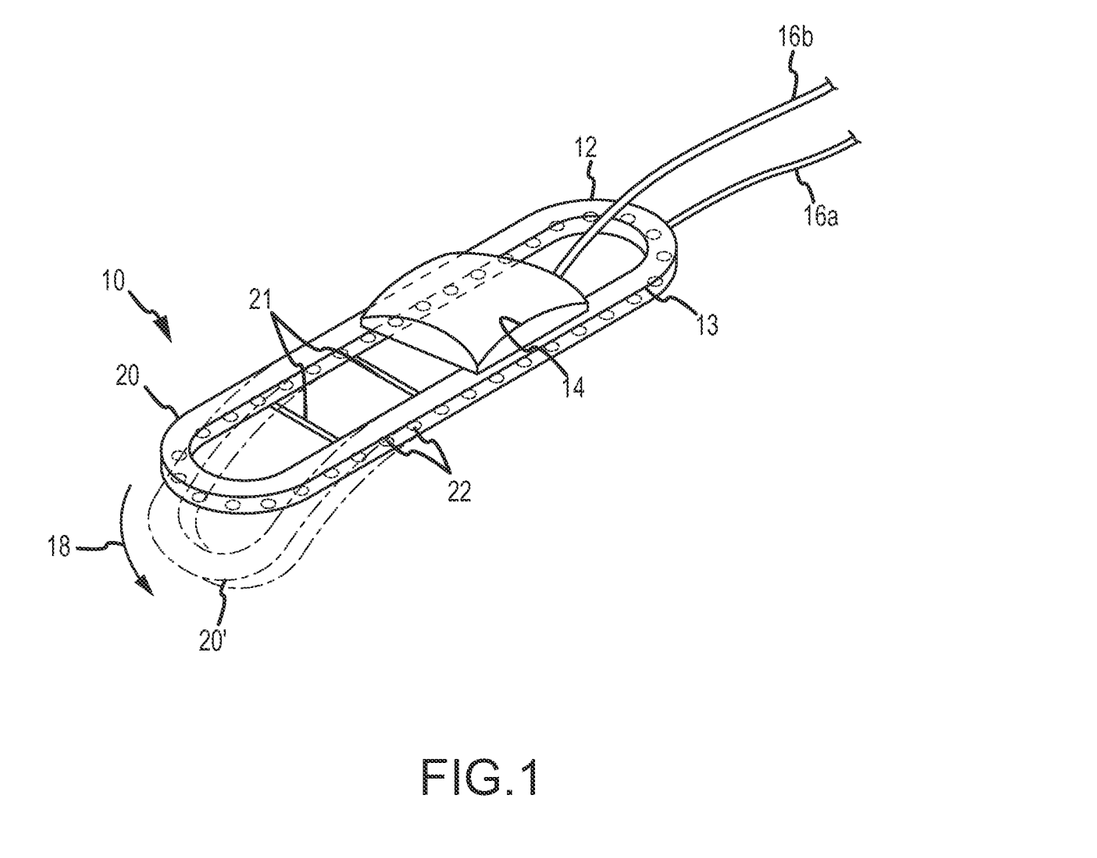
FIG. 1 is a perspective view of an exemplary embodiment of a template system.
Figure 2A:
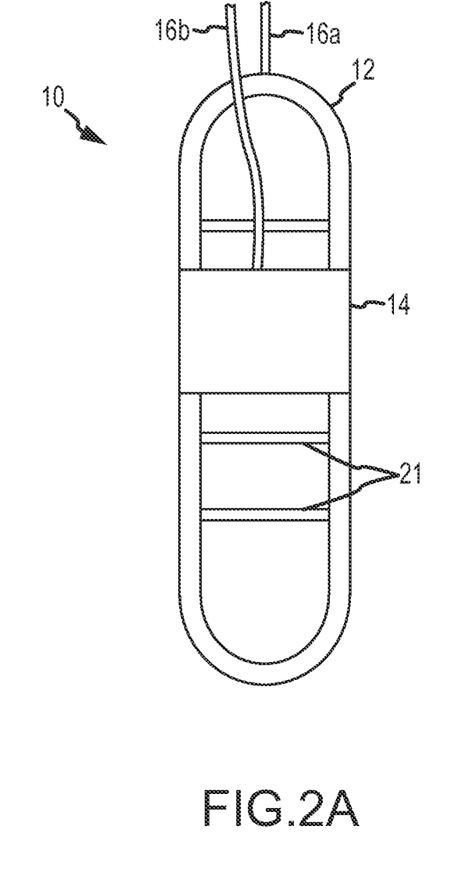
FIG. 2a-c are plan views of the exemplary template system shown in FIG. 1, wherein (a) is a top plan view, (b) is a side plan view, and (c) is a bottom plan view.
Figure 2B:
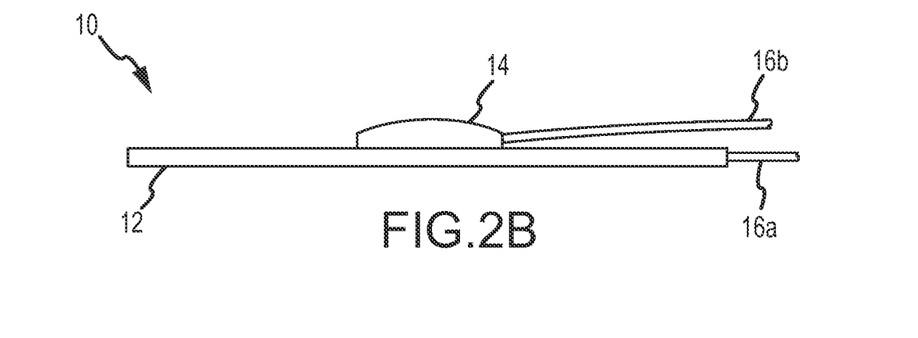
Figure 2C:
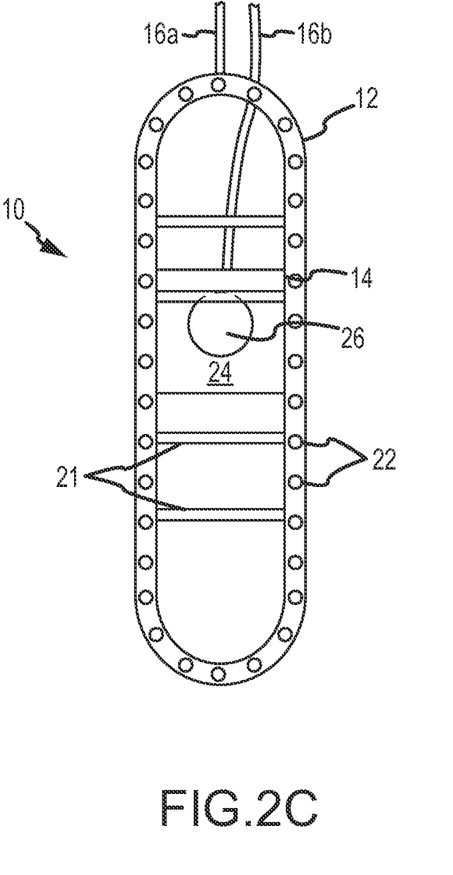

FIG. 1 is a perspective view of an exemplary embodiment of a template system 10. Various features of the template system 10 may also be seen in FIG. 2a-c. FIG. 2a-c are plan views of the exemplary template system 10 shown in FIG. 1, wherein (a) is a top plan view, (b) is a side plan view, and (c) is a bottom plan view. At the distal end, the template system 10 may include a track 12 and a transducer 14. At the proximal end, the template system 10 may be connected via umbilical 16a and 16b to other systems and devices (not shown). The transducer(s) may be ablation transducers, imaging transducers used in support of ablation, other transducers, and/or a combination of transducers.

As used herein and commonly used in the art, the term "distal" is used generally to refer to components located or generally orientated toward the heart or other tissue (the "worksite") when the template system 10 is in use. On the other hand, the term "proximal" is used generally to refer to components or portions of the template system 10, such as the handle (not shown) that are located or generally orientated away from or opposite the worksite when the template system 10 is in use.

One or more umbilical (16a and 16b are shown in FIG. 1 and FIG. 2a-c) define at least one lumen or longitudinal channel between the proximal and distal ends of the template system 10. In exemplary embodiments, wiring may be fitted through the lumen. For example, wiring may be provided for delivering electrical power or other energy (e.g., ablative energy) from one or more energy sources outside of the patient's body to the track 12 or transducer 14 positioned within the patient's body. Or for example, the wiring may be used to communicate other signals between various sensors (e.g., pressure, temperature, optical sensors, etc.) provided at the distal end of the template system with various output or feedback systems connected to the proximal end of the template system. Also in exemplary embodiments, tubing may be fitted through the lumen. For example, vacuum tubing may be provided for attaching and detaching the track 12 to tissue at the worksite. Fluid delivery tubing may also be provided for delivering a saline solution or other fluid to the worksite (e.g., to cool the tissue, a coupling fluid to form a fluid interface between the transducer and the tissue, fluid flushing, dye injection, etc.). Return lines may be provided, e.g., for removing fluid from the worksite.

In exemplary embodiments, the umbilical 16a and 16b are about two feet long, so that these may extend from a worksite at the distal end of the template system 10 inside the body (e.g., near the heart inside the sternum) to the proximal end of the template system 10 outside of the body (e.g., through the abdomen) where the wiring and tubing can be connected with various systems and devices such as a drive system, one or more fluid and vacuum control valves, and the like.

In an exemplary embodiment, umbilical 16a and 16b are fabricated from flexible resilient materials, and are preferably fabricated of materials suitable for use in humans, such as various commercial-grade polymers. Suitable polymers include those well known in the art, such as polyurethanes, polyether-block amides, polyolefins, nylons, polytetrafluoroethylene, polyvinylidene fluoride, and fluorinated ethylene propylene polymers, and other conventional materials. However, the umbilical 16a and 16b are not limited to being manufactured from any particular type of material.

The track 12 and transducer 14 may also be fabricated of (or coated with) materials suitable for use in humans, such as those described above for umbilical 16a and 16b. Preferably, the track 12 and transducer 14 are relatively small, low-profile components such that they may be readily inserted into a patient's body using minimally invasive scope-based or port-based surgery techniques. For example, the track 12 may have a width of approximately 12 mm and the transducer 14 may have a width of approximately 10-11 mm.

The transducer 14 may be pre-mounted to the track 12, e.g., during manufacture or by the user prior to use. Alternatively, track 12 and transducer 14 may be placed separately into the patient's body and the transducer 12 associated with the track 12 inside the patient's body. Such an embodiment enables the use of separate transducers (e.g., an imaging transducer and an ablative transducer). In either case, the transducer 14 is provided on the track 12 such that the transducer 14 is guided by and slides or is otherwise movable on the track 12 (see, e.g., the operation illustrated in FIG. 6b-d). The track 12 preferably provides at least some spatial and positional control for the ablation as described above.

Track 12 may include a base portion 13. The base portion 13 is shown in the figures as being substantially oval-shaped or rectangular with rounded ends. It is noted, however, that the base portion 13 may intentionally or unintentionally have a wide variety of configurations, and need not be oval-shaped. For example, manufacturing irregularities may result in the base portion 13 having a non-uniform configuration. Or for example, the base portion 13 may be intentionally selected to have different cross-sectional configurations to achieve desired results. Preferably, the shape of the base portion 13 corresponds to the configuration of the worksite so that the user only has to move the transducer 14 over the base portion 13 without having to move the transducer 14 through any particular pattern. By way of illustration, the oval-shaped base portion 13 shown in the figures may be used to form a substantially linear lesion in the tissue. Alternatively, a track 12 having a curved base portion 13 may be used if it is desired to form a curved lesion. The track 12 may also be circular, J-shaped, L-shaped, T-shaped, or any other suitable shape.

The shape of the track 12 may be retained using bridging members 21. In an exemplary embodiment, the bridging member 21 includes a plurality of support wires as shown in the figures. The support wires serve to hold the opposing sides of the base portion 13 in a substantially fixed relation to one another so that the base portion 13 does not open or spread during placement or operation of the transducer 14. Preferably, the support wires are sufficiently small in diameter so as not to interfere with energy delivery to the tissue by the tranducer. For example, the diameter may be selected such that a laser beam or ultrasound light may be focused onto the tissue beneath the support wires from either side. Alternatively, the bridging member 21 may be transparent so that energy can be focused through the bridging member and onto the tissue. Of course other mechanisms for shape retention of the base portion 13 of track 12 are also contemplated.

Preferably, the base portion 13 of track 12 is malleable or flexible so that the base portion 13 conforms to the three-dimensional shape of the tissue. In FIG. 1, for example, an end portion 20 of the track 12 is shown as it may be formed (e.g., as illustrated by arrow 18 shown in FIG. 1) into position 20'. Such flexure reduces gaps between the base portion 13 of the track 12 (and hence the transducer 14 mounted thereon) and the tissue 12. This better enables the track 12 to be anchored to the tissue during use and also serves to maintain the transducer 14 in good contact (e.g., acoustic coupling) with the adjacent tissue to be ablated. In exemplary embodiments, the base portion 13 may be manufactured of a shape-memory material such as nitinol or a shape-memory polymer so that it automatically returns to an initial state (e.g., for easy removal from the patient's body).

In an exemplary embodiment, the track 12 may be foldable. Accordingly, the track 12 is not deployed to its final shape and/or size until after it is located at the worksite. It is noted, however, that the track 12 does not need to be flexible or malleable at all. In other embodiments, the track 12 may be stiff and preformed into a desired shape at the manufacturing facility or by force applied by the user.

In any event, the track 12 may include means for attaching or anchoring the base portion 13 to the tissue. In an exemplary embodiment, this attachment is accomplished by suction applied between the base portion 13 and the tissue. For example, the base portion 13 may include one or more suction ports 22. In FIG. 1 and FIG. 2c, the suction ports 22 are spaced substantially evenly around the perimeter of base portion 13, although no such pattern is required. The suction ports 22 may be operatively associated with a vacuum (e.g., a vacuum line provided through umbilical 16a). When a vacuum is applied to the suction ports 22, the base portion 13 attaches to the tissue, thereby maintaining a constant position during a procedure. When the vacuum is released, the base portion 13 releases from the tissue and can be withdrawn from the patient's body in a conventional manner.

Figure 3:
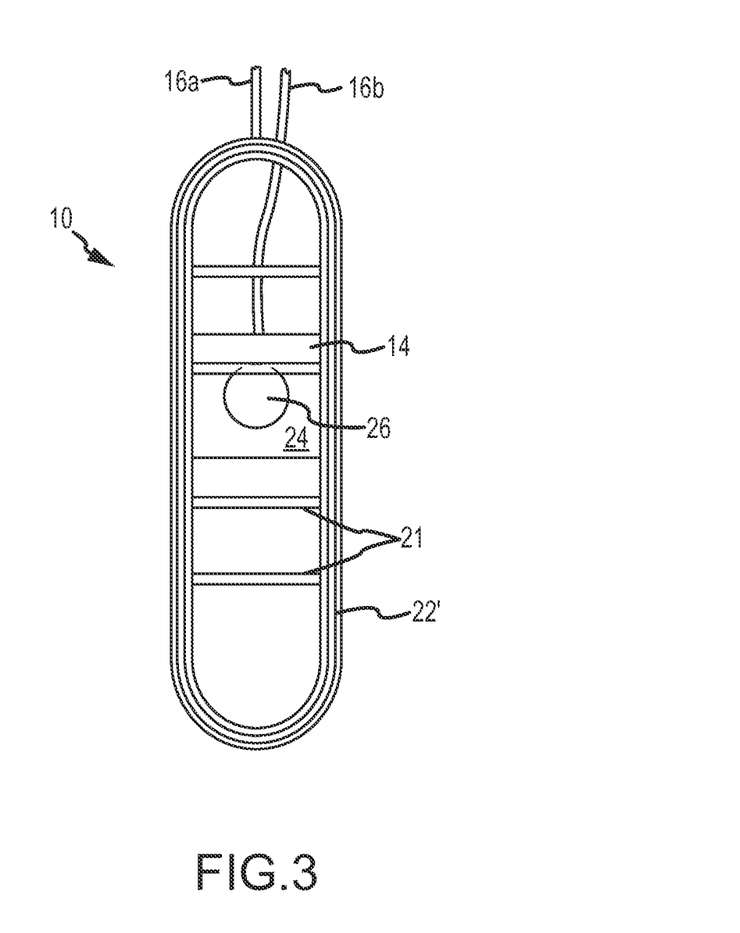
FIG. 3 is a bottom plan view corresponding to FIG. 2c showing an alternative embodiment of suction ports which may be implemented on a track of the template system.

It is noted that the attachment or anchoring means are not limited to a plurality of suction ports or other apertures. FIG. 3 is a bottom plan view of the base portion 13 shown in FIG. 2c showing an alternative embodiment. In this embodiment, the attachment or anchoring means is provided in the form of a suction channel 22' formed around the perimeter of base portion 13. Operation of the channel 22' to attach the base portion 13 of track 12 to a tissue is similar to that described above for the suction ports 22 shown in FIG. 2c.

Still other embodiments are also contemplated for anchoring the base portion 13 of the track 12 to tissue. For example, a gel gasket or adhesive may be provided between the base potion 13 and the tissue. It is also noted that the track 12 need not be anchored to the target area. In other embodiments, the track 12 may be anchored to other tissue adjacent the target area. It is only important that the track 12 be anchored or otherwise attached to the tissue for the procedure in order to serve as a guide for the transducer 14 to align and control operation of the transducer 14 so that quality lesion may be formed. Thus any track-mounting tissue may be utilized as long as it causes the mounted transducer to have the desired spatial relationship with tissue to be ablated. This might even mean that the track is suctioned to tissue opposite that to be ablated and the transducer is instead driven over the opposite face or side of the track firing away from the track into the tissue to be ablated.

Figure 4A:
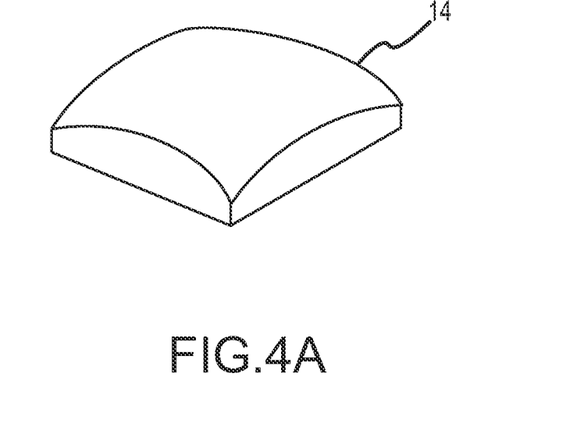
FIG. 4a is a perspective view showing an exemplary embodiment of a transducer which may be implemented with the template system.
Figure 4B:
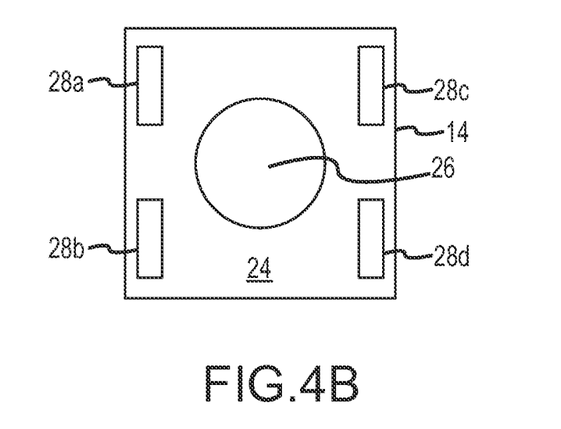
FIG. 4b is a bottom plan view of the transducer showing the transducer face.

FIG. 4a is a perspective view showing an exemplary embodiment of a transducer 14 which may be implemented with the template system 10. FIG. 4b is a bottom plan view of the transducer 14 showing the transducer face 24. The transducer 14 may be any suitable transducer depending on the desired use. For example, the transducer 14 may be an ablative transducer, an imaging transducer, etc.

In an exemplary embodiment, the transducer is a High Intensity Focused Ultrasound (HIFU) transducer. The HIFU transducer may be connected via umbilical 16b to an energy source at the proximal end. The HIFU transducer converts this energy to ultrasound signals which may be emitted from an aperture(s) 26 formed in the face 24 of the transducer 14 to form lesions in tissue at the target area.

Other exemplary transducers or ablation energy-emitters that are suitable for use with the template system 10 include, but are not limited to, laser and radio frequency (RF) devices. More than one transducer may also be used for a single procedure. For example, an acoustic imaging transducer may be used to image the target area for pre-imaging of the worksite, then an ablating transducer may be used to form ablative lesions in the tissue, and then acoustic imaging transducer may be used for post-imaging of the worksite. In an exemplary embodiment, multiple transducers may be housed together to avoid the need to insert and remove multiple transducers during the procedure. Or for example, the same transducer may be used for both imaging and lesion formation by controlling the energy output of the transducer.

Transducer 14 may also include one or more magnets 28a-d to magnetically engage the track 12. The magnets 28a-d may be provided to facilitate association of the transducer 14 with the track 12 (e.g., where multiple transducers are used with the same track during a single procedure). Magnets 28a-d may also be provided to help retain the transducer 14 on the track 12. For example, track 12 may incorporate matching attracting magnets or even be fabricated of a magnetic material such as magnetic stainless steel.

It is noted that magnets are not the only way to provide these benefits. In other embodiments, a vacuum may help associate the transducer 14 with the track 12. In still other embodiments, a wide variety of features (e.g., cog, latch, roller, bearing, sliding bearing, etc.) may be provided on the transducer 14 and engage corresponding features on the track 12 (e.g., guide rails).

Movement of the transducer 14 along the track 12 may be effected using any of a wide variety of implementing features, e.g., generally referred to herein as a drive system for the transducer. The drive system may include a driving wire, cord or chain which rotates or is pushed or pulled. The drive system may also include any type of driving motor or actuator which may be situated at or near the track, on the transducer, or away from the track or external to the patients body (e.g., utilizing a driving wire). For example, the transducer 14 may be dragged (or even pushed) along the track 12 using an inexpensive, disposable guide wire (e.g., a mechanical pull/push wire, a rotational driving wire, etc.). The rate of movement of the transducer 12 may be monitored as by monitoring the wire motion or rotation with a sensor or by having positional indices on the track to encode the position. Accordingly, movement of the transducer may be continuous or to one or more positions where the transducer is stopped at least temporally.

Figure 5:
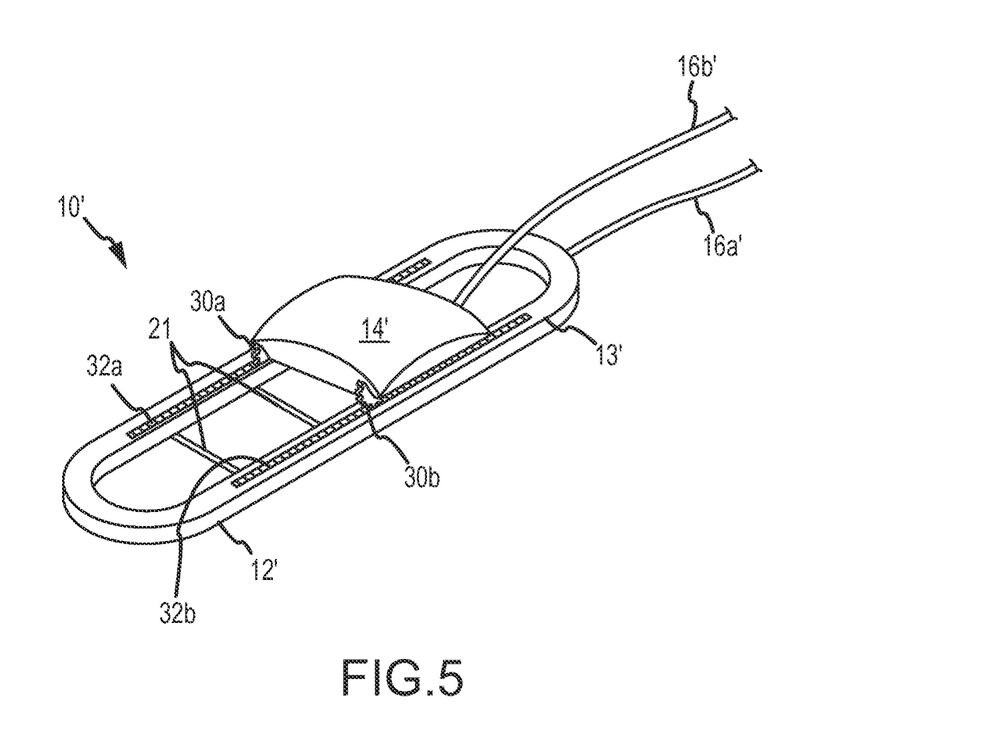
FIG. 5 is a perspective view of another embodiment of a template system showing a gear wheel on the transducer engaging a gear strip on the track to move the transducer along the track.

FIG. 5 is a perspective view of another embodiment of a template system 10' showing gear wheels 30a-b on the transducer rotationally engaging gear strips or toothed rails 32a and 32b, respectively on the track 12' to move the transducer 14' along the track 12'. The gear system helps maintain alignment of the transducer 14' and may also serve to index movement of the transducer 14' along the length of track 12' so that the user can better pace movement of the transducer 14'. A drive motor (not shown) may also be implemented with the gear system, enabling the physician to control the rate of movement of the transducer.

It should also be noted that the template system 10 may also implement a wide variety of different sensing means to provide additional feedback (e.g., contact assessment with the tissue) to the user during the procedures. A wide variety of these types of sensors suitable for use with the template system 10 are well known in the art. Exemplary sensors include but are not limited to piezoelectric, pressure, thermistor, thermocouple, or ultrasound sensors. More than one sensor or type of sensor may also be implemented.

Electrical wiring may be provided to extend through the lumen of the umbilical 16a and 16b to enable these and other sensors. The electrical wiring may convey electrical signals from the sensor(s) to a data acquisition/processing/output device (also not shown), such as, e.g., an electrophysiological sensing electrode or device. Alternatively, a wireless connection may be implemented, e.g., by providing a transmitter in the track/transducer and a receiver in association with the data acquisition/processing/output device. Accordingly, the electrical signals from the sensor(s) may be viewed by the user, e.g., as output on an electrical monitoring device. The resulting electrical signal may be processed and/or otherwise output for the user during the procedure.

It is noted that any suitable analog and/or digital device may be implemented for outputting the electrical signals generated by the sensor(s) to a user. In addition, the electrical signals may be further characterized using a suitable processing device such as, but not limited to, a desktop or laptop computer. Such processing device may be implemented to receive the voltage signal generated by the contact assessment sensor(s) and convert it to a corresponding contact condition and output for the user, e.g., at a display device, an audio signal, or tactile feedback or vibrations on the handle of the catheter. In any event, circuitry for conveying output of the piezoelectric sensor to a user in one form or another may be readily provided by those having ordinary skill in the electronics arts after becoming familiar with the teachings herein.

Although specific designs of template system 10 have been described, other designs of the template system 10 may also be implemented as will be readily understood by those having ordinary skill in the art after becoming familiar with the teachings herein. For example, one or more of the components of template system 10 may be disposable. The particular types and configuration of components used for the template system 10 will depend at least to some extent on design considerations. Exemplary design considerations may include, but are not limited to, the material and desired structural properties, the length, shape, and cross-sectional area of the components. And of course, the design parameters may be different for various procedures or physician preferences.

Figure 6A:
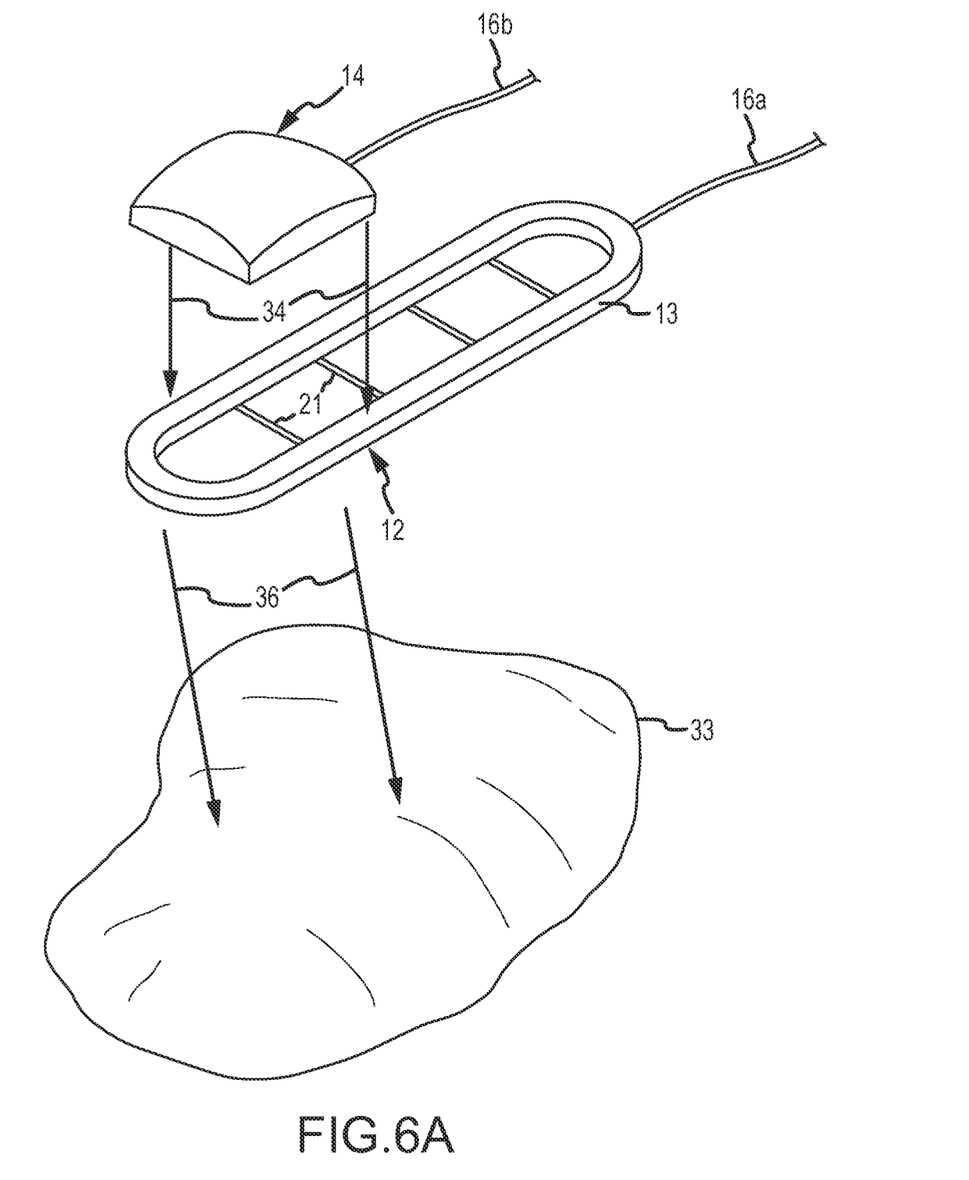
FIG. 6a is a perspective view showing an exemplary embodiment of a track which may be implemented with the template system.

Having described exemplary embodiments of template system 10 above, use of the template system 10 will now be described with reference to FIGS. 6a-d. FIG. 6a is a perspective view showing an exemplary embodiment of a track 12 and transducer 14 which may be implemented with the template system 10 as these components may be inserted into a patient's body, e.g., adjacent heart tissue 33.

During an exemplary procedure, the transducer 14 may be attached to the track 12 (e.g., as illustrated by arrows 34 shown in FIG. 6a) and the track 12 and transducer 14 positioned adjacent the target area or worksite. In an exemplary embodiment, the transducer 14 may be attached to the track 12 outside of the patient's body and both components positioned inside the patient's body together. In other embodiments, the track 12 may be pre-positioned in the patient's body and the transducer 14 may then be inserted separately and associated with the track 12 (e.g., as illustrated by arrows 34 shown in FIG. 6*a*) inside the patient's body. In this second mode a self-aligning (e.g., magnetic) attachment of transducer 14 to track 12 enables blind mating of the two components.

In any event, the track 12 and transducer 14 may be positioned at the appropriate location adjacent the target area or worksite using conventional surgical techniques (e.g., the use of scope-based and port-access surgical tools). Although many applications of the inventive device will be minimally invasive, the present invention may also be used open surgery procedures.

For purposes of illustration where the worksite is tissue on the heart 33, an incision may be made in the patient's body beneath the rib cage during a minimally invasive surgery. An endoscope may be inserted through the incision and directed toward the heart to visually aid the physician in locating the worksite. Once the worksite has been located, the track 12 and transducer 14 may be inserted (either together or separately) into the patient's body and moved into position. In an exemplary embodiment, the track 12 and transducer 14 may be delivered to the worksite using a wand having a magnetic tip which engages a magnetic feature on the track and/or transducer.

Once positioned adjacent the worksite, the track 12 may be anchored or otherwise attached to tissue adjacent the worksite (e.g., as illustrated by arrows 36 shown in FIG. 6*a*). In an exemplary embodiment, the track 12 may be attached to tissue adjacent the worksite by applying a vacuum to one or more suction ports in the base portion 13 of the track 12. Although the track 12 is shown as it may be attached to tissue on the heart 33 surrounding the worksite, it is noted that in other embodiments the track 12 may be attached to other tissue adjacent the worksite (e.g., an opposed tissue surface).

Figure 6B:
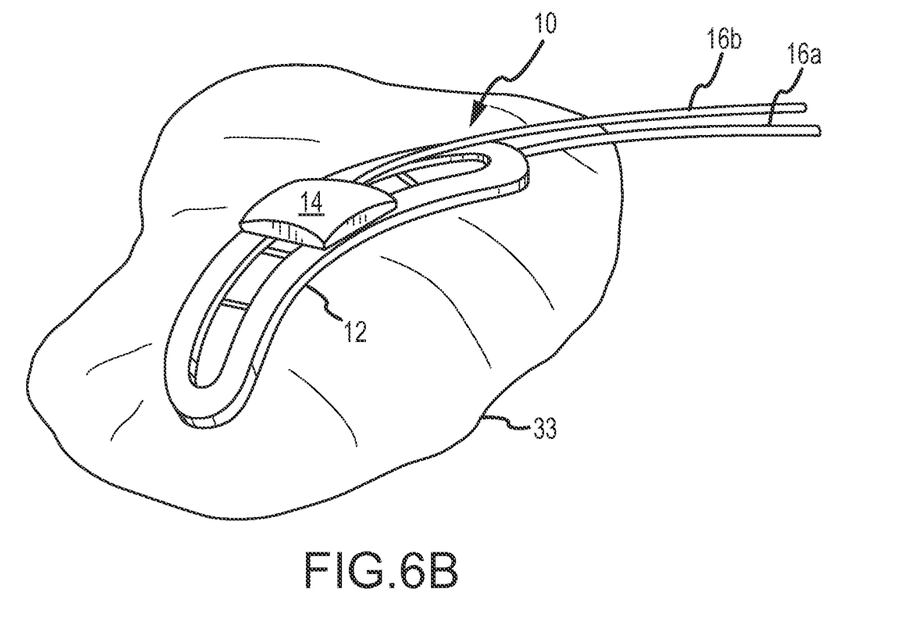
FIG. 6b-d are perspective views of the template system as it may be used on tissue on an outer surface of a heart, wherein (b) shows the transducer in a first position, (c) shows the transducer in a second position, and (d) shows the transducer in a third position.
Figure 6C:
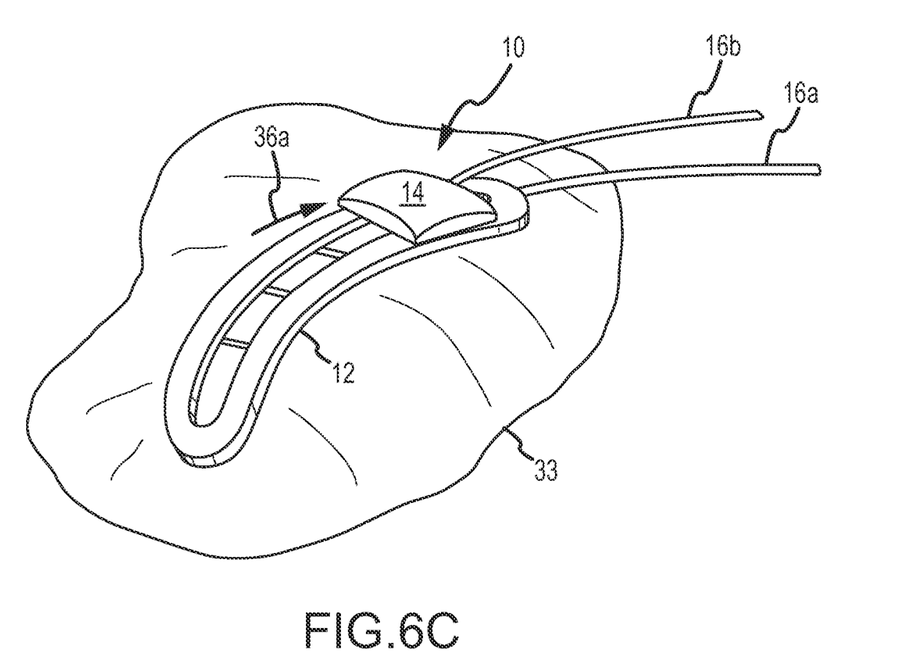
Figure 6D:
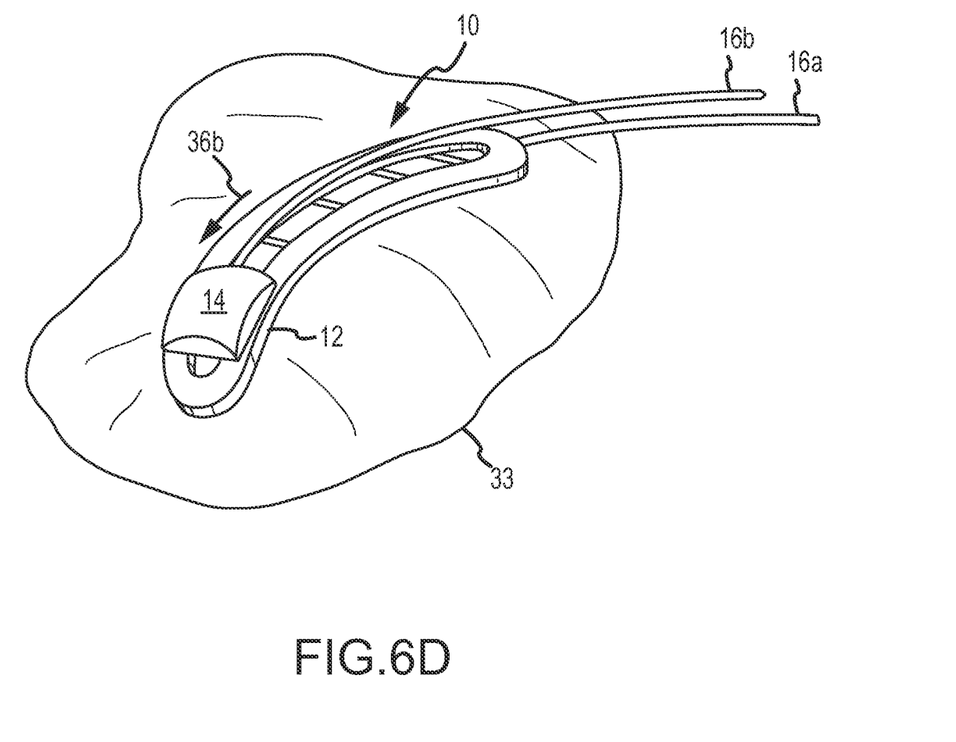

Once the track 12 and transducer 14 has been properly positioned and the track 12 has been attached at the desired location, the template system 10 may be used to perform various procedures (e.g., imaging, ablation, and other procedures). FIG. 6*b-d* are perspective views of the template system 10 as it may be used on tissue on an outer epicardial surface of a heart 33 wherein (b) shows the transducer 14 in a first position, (c) shows the transducer 14 as it may be moved in the direction illustrated by arrow 36*a* to a second position, and (d) shows the transducer 14 as it may be moved in the direction illustrated by arrow 36*b* to a third position.

During operation, the transducer 14 may be moved along the track 12 (e.g., in the directions of arrows 36*a* and 36*b* to the different positions illustrated in FIG. 6*b-d*) using any of a variety of different mechanisms, such as the guide wire or drive motor discussed above. The transducer 14 may be actuated for imaging, or delivery of ablative or other therapeutic energy to the tissue as the transducer 14 is moving along the track 12 or as it is stopped at fixed or sequential positions along the track. For example, an imaging transducer may be used to pre-scan the worksite after placement of the track 12 to help ensure its proper and preferably safe position for the procedure. Likewise, an ablative transducer may be used to form lesions in the tissue. The imaging transducer may be used again to post-scan the worksite to ensure the desired lesion has been formed. Of course other transducers may also be implemented for a wide variety of different procedures, and the particular use of template system 10 is not limited to the embodiments shown and described herein.

It will be readily appreciated to those having ordinary skill in the art, after becoming familiar with the teaching herein, that the template system enables a wide variety of features and benefits for the user and the patient. For example, having the track anchored or otherwise attached adjacent the worksite keeps the transducer from moving outside the bounds of the target area. This reduces or altogether eliminates damage to surrounding tissue and helps ensure the user forms quality lesions, such as continuous unbroken extended lesions, a spot lesion or series of spot lesions, or a closed-path lesion. The template system also provides a certain level of control for the user. For example, indexing movement of the transducer on the track helps ensure that only the desired amount of energy is delivered to the tissue during moving ablation. The use of imaging transducers also enables the user to visually inspect a target area which may otherwise be difficult to see using conventional imaging techniques such as endoscopes. These, and other features of the template system, are particularly desirable where the tissue may be moving (e.g., the beating heart).

Before continuing, it is noted that the template system 10 has been described as it may be used for procedures in the vicinity of the heart. The template system 10, however, is not limited to such procedures, and may be used for procedures involving other target tissue in other areas of the body.

It is noted that the track 12 may also include integrated powering electrodes (not shown) which enable the transducer to receive power from the track rather than from a separate umbilical 16*b*. It is also noted that the known practice of utilizing a fluid-filled acoustically-transparent membrane or standoff between the transducer and the target tissue may also be implemented in order to enhance acoustic coupling of transducer 14 to tissue 33, e.g., to help cool the transducer and/or even tissues not being ablated at that moment, or to set a desired transducer working distance to tissue.

Although several embodiments of this invention have been described above with a certain degree of particularity, those skilled in the art could make numerous alterations to the disclosed embodiments without departing from the spirit or scope of this invention. References are only used for identification purposes to aid the reader's understanding of the present invention, and do not create limitations as to the position, orientation, or use of the invention. In addition, various combinations of the embodiments shown are also contemplated even if not particularly described. Changes in detail or structure, such as but not limited to combinations of various aspects of the disclosed embodiments, may be made without departing from the spirit of the invention as defined in the appended claims.

What is claimed is:

1. A template system for use in a medical procedure comprising:

a track comprising a base portion and at least one suction port, the at least one suction port configured to anchor the track to a tissue after the track is positioned adjacent a target area inside a patient's body, wherein the track is foldable for deployment to a worksite, and unfoldable to a final shape and size after being located at the worksite inside the patient's body;

at least one stationary shape retaining bridging member spanning from a first side of the base portion to another side of the base portion across an opening formed through the base portion of the track; and a transducer operatively associatable with the track, the transducer configured to be guided by the track adjacent the target area while the transducer is moved along the track for the medical procedure, wherein the bridging member maintains a predetermined shape of the opening in the base portion of the track when the transducer is removed from the track.

2. The system of claim 1, further comprising an umbilical attached to the track, the umbilical configured to provide a conduit to the track for application of a vacuum to the at least one suction port.

3. The system of claim 1, further comprising an umbilical attached to the transducer, the umbilical configured to provide a conduit to the transducer for energy delivery.

4. The system of claim 1, further comprising an umbilical attached to the transducer, the umbilical configured to provide a conduit to the transducer for fluid delivery.

5. The system of claim 1, further comprising a wired drive system configured to move the transducer along the track, wherein the drive system is configured to engage the transducer to the track to move the transducer along the track.

6. The system of claim 1, further comprising an umbilical attached to the transducer, the umbilical configured to provide a conduit extending outside of a patient's body for at least one driving wire, the at least one driving wire operable to control movement of the transducer on the track.

7. The system of claim 1, wherein the at least one suction port comprises at least one channel in a bottom surface of the track.

8. The system of claim 1, wherein the at least one bridging member includes a plurality of stationary support wires spanning the opening formed through the base portion, to maintain a predetermined width of the track during use.

9. The system of claim 1, wherein the track is flexible in at least one plane to substantially conform to a shape of the tissue during use.

10. The system of claim 1, wherein the track and the transducer each include at least one magnetic material configured to mutually develop magnetic forces to facilitate mating of the track with the transducer.

11. The system of claim 1, further comprising a fluid delivery port near a face of the transducer.

12. The system of claim 11, wherein the fluid delivery port is operable to provide a fluid interface between the transducer and the target area, said interface comprising a fluid filled membrane.

13. The system of claim 11, wherein the fluid delivery port is operable to cool at least one of the target area or the transducer.

14. The system of claim 1, further comprising a gear wheel on the transducer and a gear strip on the track, the gear wheel configured to engage the gear strip after the transducer is mounted to the track to move the transducer along the track.

15. The system of claim 14, further comprising an actuator operatively associated with the gear wheel on the transducer, the actuator operable to move the transducer along the track at a predetermined pace for a known distance.

16. The system of claim 1, wherein the transducer is selected from the group consisting of an ablation transducer, an imaging transducer, and a combination transducer for ablation and imaging.

17. The system of claim 1, wherein the transducer is separable from the track, the transducer configured to be mounted on the track after the track is anchored to the tissue.

18. A method of treatment comprising:
folding and inserting a track into a patient's body and positioning the track adjacent a target area inside the patient's body, wherein the track unfolds to a final shape and size after being located inside the patient's body;
anchoring the track to a tissue in the target area;
positioning a transducer guided by the track adjacent the target area to perform a medical procedure; and
passing at least one driving wire into the patient's body to engage the transducer to the track and extendable outside of a patient's body for controlling a movement, position, or orientation of the transducer on the track.

19. The method of claim 18, further comprising passing a conduit to the track for application of a vacuum to at least one suction port on the track for anchoring the track to the tissue.

20. The method of claim 18, further comprising passing a conduit to the transducer for delivering energy to the transducer.

21. The method of claim 18, further comprising passing a conduit to the transducer for delivering fluid to the tissue or transducer.

22. The method of claim 18, further comprising mating the track and the transducer.

23. The method of claim 18, further comprising driving the transducer along the track.

24. A system for use in a medical procedure comprising:
means for attaching adjacent a target area inside a patient's body, wherein the means for attaching is foldable for deployment to a worksite, and unfoldable to a final shape and size after being located at the worksite inside the patient's body;
means for anchoring the means for attaching to a tissue after the means for attaching is positioned adjacent the target area; and
means for delivering energy to the target area from two or more positions along the means for attaching, the means for delivering energy mounted on the means for attaching after the means for attaching is anchored to the tissue.

25. The system of claim 24, further comprising means for providing a conduit to the means for attaching.

26. The system of claim 24, further comprising means for providing a conduit to the means for delivering energy.

27. The system of claim 24, further comprising means for maintaining a predetermined shape of the means for attaching in at least one dimension.

28. The system of claim 24, further comprising means for conforming the means for attaching to the tissue.

29. The system of claim 24, further comprising means for mating the means for attaching with the means for delivering energy.

30. The system of claim 24, further comprising means for moving the means for delivering energy at a controlled pace.

* * * * *